United States Patent [19]
Hosler

[11] 3,987,120
[45] Oct. 19, 1976

[54] RECOVERY OF MESITYLENE AND ETHYLTOLUENES FROM PETROLEUM NAPHTHA REFORMATE

[75] Inventor: Peter Hosler, Wallingford, Pa.

[73] Assignee: Sun Oil Company of Pennsylvania, Philadelphia, Pa.

[22] Filed: May 1, 1975

[21] Appl. No.: 573,499

[52] U.S. Cl. ..................... 260/674 A; 260/674 R
[51] Int. Cl.² ................................ C07C 7/01
[58] Field of Search ................ 260/674 A, 674 R

[56] References Cited
UNITED STATES PATENTS

| | | |
|---|---|---|
| 2,774,800 | 12/1956 | Shmidl et al. .................. 260/674 |
| 2,873,300 | 2/1959 | Corson et al. ................... 260/674 |
| 2,943,121 | 6/1960 | Spence ........................... 260/674 |
| 3,189,659 | 6/1965 | Newton ........................... 260/674 |

*Primary Examiner*—Delbert E. Gantz
*Assistant Examiner*—C. E. Spresser
*Attorney, Agent, or Firm*—J. Edward Hess; Donald R. Johnson; Paul Lipsitz

[57] ABSTRACT

A process for recovering mesitylene and ethyltoluenes contained in a petroleum naphtha reformate by sulfonating the naphtha reformate with sulfuric acid and hydrolyzing the sulfonate product at reduced pressure.

3 Claims, No Drawings

RECOVERY OF MESITYLENE AND ETHYLTOLUENES FROM PETROLEUM NAPHTHA REFORMATE

In commercial reforming of petroleum naphtha valuable aromatic compounds are formed. Some of these aromatics such as benzene, toluene, the xylenes and ethyl benzene are readily recovered as high purity chemical intermediates by conventional methods of extraction and distillation. Also present in the reformate, however, are nine-carbon aromatic compounds and these include pseudocumene, mesitylene (1,3,5-trimethylbenzene) and ethyltoluene. In commercial practice only pseudocumene can be recovered from the reformate in high purity by distillation. It would be highly desirable to be able to economically separate the mesitylene and ethyltoluene in a petroleum naphtha reformate as these are intermediates to useful chemicals. For example, mesitylene has utility as an intermediate to tri-mesic acid and is also useful as an octane improving additive in gasoline. Ethyltoluene is an intermediate to vintyltoluene. Mesitylene has a boiling point of about 165° C. and the isomeric ethyltoluenes boil over a range of from 150°to 165° C. Thus, separation of these compounds is difficult.

An object of this invention is to provide a practical and economical means of separating mesitylene and ethyltoluenes in high purity from other nine carbon aromatics which are present in petroleum naphtha reformate. In addition, the method of the invention, provides a useful solvent from the aromatic hydrocarbons remaining after processing the petroleum naphtha reformate. In accord with the invention, mesitylene and ethyltoluenes are recovered from a petroleum naphtha reformate by sulfonating said naphtha reformate with sulfuric acid, hydrolyzing the sulfonate product under vacuum conditions, and distilling from the hydrolysis mass mesitylene and ethyltoluene product.

It is known in the art that mesitylene alone can be recovered from liquid nine-carbon atom aromatic hydrocarbon fractions by sulfonation. For example, U.S. Pat. No. 3,189,659 discloses a method of obtaining mesitylene from $C_9$ aromatic hydrocarbon fraction by sulfonating a $C_9$ aromatic hydrocarbon fraction containing between about 25% and 40% mesitylene to form the sulfonic acid derivatives of the $C_9$ aromatics, then reforming mesitylene by selectively hydrolyzing mesitylene sulfonic acid at atmospheric pressure to mesitylene to the exclusion of the other $C_9$ aromatics, and subsequently separating the resultant product from the remaining $C_9$ sulfonic acids, such as, by selective extraction. However, the method does not lend itself to obtaining ethyltoluene from the mixture. Furthermore, the method of the patent does not lend itself to a petroleum naphtha of relatively low mesitylene content, as, for example, a content of about 19% to 20% mesitylene, as is found in certain refinery naphtha reformates. Likewise, U.S. Pat. No. 2,873,300 discloses a selective sulfonation procedure for separating mesitylene and other trialkylbenzenes in rather high concentration from benzene hydrocarbons by subjecting a mixture of alkylbenzenes containing the mesitylene to sulfonation with a stoichiometric excess of concentrated sulfuric acid over that needed to sulfonate the other alkylbenzenes so that sulfonation of the other hydrocarbons takes place to the substantial exclusion of the mesitylene. The unsulfonated 1,3,5-trialkylbenzene is thus readily separated from the mixture. However, the process of this patent also cannot economically accomodate mixtures where the amount of mesitylene is low because the small amounts of mesitylene become essentially all dissolved in the sulfonate phase and it cannot be readily separated therefrom. Furthermore the process does not provide means for recovering purified ethyltoluene as well as mesitylene. Other mesitylene separation methods are known, but, like the above processes do not enable both mesitylene and ethyltoluene to be obtained.

In carrying out the process of the invention any source of nine-carbon aromatics may be used, but, preferably, the source of such nine-carbon aromatics will be a distillate cut taken from the aromatic extract of naphtha reformate. The cut is taken after benzene, toluene and xylenes have been removed, but before pseudocumene is distilled. A typical cut used to advantage in the process of the invention is known as pseudocumene pre-fractionation overhead and has the following typical analysis:

|  | Wt. % | Boiling Point, °C |
|---|---|---|
| o-xylene | 0.8 | 144.41 |
| Cumene | 4.0 | 152.39 |
| n-Propylbenzene | 11.8 | 159.22 |
| 3-Ethyltoluene | 33.0 | 161.31 |
| 4-Ethyltoluene | 16.1 | 161.99 |
| Mesitylene | 18.3 | 164.72 |
| 2-Ethyltoluene | 13.6 | 165.15 |
| Pseudocumene | 2.4 | 169.35 |

In accord with the invention the pseudocumene pre-fractionation overhead is mixed with concentrated sulfuric acid at elevated temperature in order to effect sulfonation. The acid used will generally be of a concentration of between about 60% to 95% $H_2SO_4$ and the temperatures employed will range from about 75° C. to about 125° C., these sulfonation conditions being conventional in the art. After sulfonation has occurred the reaction mass is cooled, generally to about 70°to 90° C., preferably about 80° C., and the acid concentration adjusted by the addition of water to 60% to about 80%, preferably about 70% acid concentration. Then vacuum is applied and the reaction mass vacuum distilled at a pressure of from about 1 to about 100 mm of mercury, preferably at about 80° C. and at about 50 mm Hg whereby selective release of the mesitylene occurs due to hydrolysis. During the vacuum distillation the acid concentration is preferably held constant by the addition of water to the distillation chamber. When the mesitylene removal is essentially completed as indicated by a reduced rate of distillation, the temperature is raised to be between about 120° and about 140° C., preferably about 130° C. and distillation continued at reduced pressure (from about 1 to about 600 mm Hg, preferably about 250 mm). One or more intermediate cuts may be taken and then the ethyltoluene distills over in good purity, but may be further purified by subsequent distillation. After removal of the ethyltoluene, the temperature may be raised further (up to about 180° C.) to hydrolyze any remaining aromatics and this hydrolyzed product is a useful industrial solvent of particular value because the mesitylene, which is a troublesome smog former, has been removed.

It will also be understood, that the diluted sulfuric acid formed may be reused by adding fuming sulfuric acid to bring it up to the desired strength. Also it will be understood that residues may be recycled in the process.

In order to further exemplify and illustrate the process of the invention the following examples are given:

hydrolysis of the sulfonic acids was done at atmospheric pressure. The results obtained are given in Table II. As can be seen from the data, a poor selectivity was observed.

TABLE II

ATMOSPHERIC HYDROLYSIS OF SULFONIC ACIDS

| Cut | 1 | 2 | 3 | 4 | 5 | 6 | 7 | 8 | 9 | 10 | 11 |
|---|---|---|---|---|---|---|---|---|---|---|---|
| Product Off, ml. | 60 | 30 | 36 | 32 | 30 | 30 | 30 | 28 | 30 | 30 | 39 |
| Total Product | 60 | 90 | 126 | 158 | 188 | 218 | 248 | 276 | 306 | 336 | 375 |
| Water Off, ml. | 23 | 33 | 41 | 48 | 57 | 68 | 81 | 99 | 169 | 199 | 237 |
| Water Added, ml. | 80 | 80 | 90 | 110 | 130 | 150 | 175 | 195 | 250 | 250 | 250 |
| Temp, °C. | 144 | 146 | 145 | 144 | 143 | 142 | 144 | 159 | 164 | 168 | 192 |
| ANALYSIS | | | | | | | | | | | |
| Toluene | — | — | — | — | — | — | — | — | — | — | 0.4 |
| Xylene | 0.3 | 0.4 | 0.3 | 0.2 | 0.2 | 0.2 | 0.2 | 0.4 | 1.6 | 1.1 | 0.9 |
| Cumene | 0.8 | 0.7 | 0.7 | 0.7 | 0.6 | 0.6 | 2.2 | 0.9 | 4.0 | 7.8 | 12.8 |
| Propyl Benzene | 1.8 | 1.9 | 2.0 | 2.0 | 2.0 | 2.0 | 2.0 | 3.2 | 12.4 | 23.0 | 36.6 |
| 3- & 4-Ethyltoluene | 56.4 | 61.0 | 60.4 | 59.7 | 59.4 | 59.7 | 58.3 | 62.9 | 54.8 | 46.9 | 32.5 |
| Mesitylene | 38.4 | 30.6 | 30.8 | 31.2 | 31.0 | 30.1 | 27.7 | 18.0 | 0.9 | — | — |
| 2-Ethyltoluene | — | 2.7 | 3.1 | 3.3 | 3.5 | 3.7 | 4.8 | 8.5 | 23.3 | 20.6 | 16.6 |
| Pseudocumene | 2.3 | 2.7 | 2.7 | 2.9 | 3.3 | 3.7 | 4.5 | 6.1 | 3.0 | 0.6 | 0.2 |
| Other | — | — | — | — | — | — | 0.3 | — | — | — | — |

EXAMPLE 1

About 3 moles (425 ml) of pseudocumene pre-fractionation overhead is stirred with 334 ml (about 6 moles) of 96% sulfuric acid for two hours at 110° C. to give the sulfonic acids. The reaction is then cooled to 80° C., and the acid concentration adjusted with water to 70%. Acid concentration may be determined on a sample of the unreacted sulfuric acid, which forms a heavy layer in the reaction mixture. The reaction is vacuum distilled at 80° C. and at about 50 mm, to give selective release of mesitylene (cuts 1 & 2, Table I). Throughout the reaction water is added to maintain a sulfuric acid concentration of about 70%. When mesitylene removal is essentially complete, as shown by a diminished distillation rate, the temperature is raised to 130° C., and the distillation is continued at about 250 mm. After an interim cut (cut 3), selective hydrolysis gives ethyltoluenes of 90% purity (cuts 4, 5, 6 & 7). The interim cut may be added to a subsequent batch to recover the mesitylene and ethyltoluenes. After most of the ethyltoluenes have been selectively hydrolyzed, the temperature is raised as required (up to about 180° C.) to hydrolyze the remaining aromatics (cuts 8 to 13). Products recovered from the process are: mesitylene, 16.5 vol. %; interim cut, 7.8%; ethytoluenes, 25.9%; solvents, 43.3%; total 93.5%.

It is also clear from a comparison of Table I and II that the use of a vacuum hydrolysis in accord with the invention unexpectedly enables a sharp separation of mesitylene and ethyltoluene by selective hydrolysis. This is evident by noting in Table I that cuts 1 to 3 are essentially all mesitylene and high concentration of ethyl toluene appear in cuts 4 to 7. In the control example (Table II) this sharp break does not occur.

The invention claimed is:

1. A process for recovering mesitylene and ethyltoluenes contained in a petroleum naphtha reformate which comprises sulfonating said naphtha reformate with concentrated sulfuric acid at a temperature between about 75° C. and about 125° C., cooling the sulfonation mass to a temperature of from about 70° C. to about 90° C., adjusting the acid concentration with water to between about 60% and about 80%, distilling the reaction mass at a pressure of from about 1 to about 100 mm. of mercury whereby hydrolysis occurs and mesitylene is taken overhead, raising the temperature to between about 120° C. and 140° C. and continuing distillation at a pressure of from about 1 to about 250 mm. whereby ethyltoluene is taken overhead.

2. The process of claim 1 where the acid concentration during the vacuum distillation is held constant by the addition of water.

TABLE I

VACUUM HYDROLYSIS OF SULFONIC ACIDS

| Cut | 1 | 2 | 3 | 4 | 5 | 6 | 7 | 8 | 9 | 10 | 11 | 12 | 13 |
|---|---|---|---|---|---|---|---|---|---|---|---|---|---|
| Product, ml | 32 | 70 | 90 | 123 | 152 | 182 | 210 | 244 | 274 | 304 | 334 | 364 | 394 |
| Water Off, ml | 4 | 15 | 31 | 49 | 62 | 81 | 121 | 198 | 272 | 320 | 412 | 470 | 664 |
| Water Added, ml | 60 | 80 | 120 | 150 | 190 | 220 | 260 | 310 | 440 | 510 | 575 | 650 | 830 |
| Temp, °C. | 75 | 81 | 114 | 126 | 125 | 130 | 130 | 146 | 150 | 150 | 154 | 170 | 176 |
| Press., mmHg | 50 | 50 | 75 | 250 | 250 | 250 | 250 | 250 | 500 | 500 | 600 | 760 | 760 |
| Analysis, Wt. % | | | | | | | | | | | | | |
| Xylenes | 0.4 | — | 0.1 | 0.3 | 0.2 | 0.2 | 0.2 | 0.7 | 1.2 | 1.9 | 1.9 | 2.2 | 1.7 |
| Cumene | — | — | — | 0.2 | 0.2 | 0.2 | 0.3 | 1.4 | 4.2 | 5.6 | 8.4 | 11.5 | 16.4 |
| Propyl Benzene | 0.1 | 0.1 | 0.1 | 0.5 | 0.7 | 0.7 | 1.0 | 4.3 | 13.3 | 16.7 | 25.4 | 33.7 | 46.3 |
| 3- & 4-Ethyltoluene | 1.4 | 2.0 | 41.6 | 90.3 | 91.9 | 90.0 | 89.1 | 82.7 | 65.8 | 51.4 | 37.2 | 18.2 | 7.7 |
| Mesitylene | 98.1 | 97.8 | 52.9 | 3.2 | 0.8 | 0.4 | 0.1 | 0.2 | — | — | — | — | — |
| 2-Ethyltoluene | — | — | 0.9 | 0.8 | 1.2 | 1.6 | 2.4 | 7.5 | 13.7 | 23.7 | 27.0 | 34.4 | 27.5 |
| Pseudocumene | — | 0.1 | 4.4 | 4.7 | 5.0 | 6.9 | 6.9 | 3.2 | 1.8 | 0.7 | 0.1 | — | 0.1 |

EXAMPLE 2

The sulfonation of Example 1 was repeated, but the

3. The process of claim 2 where the petroleum naphtha reformate is a pseudocumene pre-fractionation overhead.

* * * * *